United States Patent
Kravitz et al.

(10) Patent No.: US 10,184,870 B2
(45) Date of Patent: Jan. 22, 2019

(54) VIBRATORY SENSOR AND METHOD

(71) Applicant: Micro Motion, Inc., Boulder, CO (US)

(72) Inventors: Andrew S. Kravitz, Erie, CO (US); Craig B McAnally, Thornton, CO (US)

(73) Assignee: Micro Motion, Inc., Boulder, CO (US)

(*) Notice: Subject to any disclaimer, the term of this patent is extended or adjusted under 35 U.S.C. 154(b) by 255 days.

(21) Appl. No.: 14/778,022

(22) PCT Filed: Apr. 3, 2013

(86) PCT No.: PCT/US2013/035154
§ 371 (c)(1),
(2) Date: Sep. 17, 2015

(87) PCT Pub. No.: WO2014/163635
PCT Pub. Date: Oct. 9, 2014

(65) Prior Publication Data
US 2016/0109345 A1   Apr. 21, 2016

(51) Int. Cl.
*G01N 9/00* (2006.01)
*G01N 11/16* (2006.01)
(Continued)

(52) U.S. Cl.
CPC .......... *G01N 9/00* (2013.01); *G01F 1/05* (2013.01); *G01F 1/66* (2013.01); *G01F 1/86* (2013.01);
(Continued)

(58) Field of Classification Search
None
See application file for complete search history.

(56) References Cited

U.S. PATENT DOCUMENTS 3,110,890 A * 11/1963 Westcott ............. G01F 23/2966
331/139
3,266,311 A * 8/1966 Andreasen .......... G01F 23/2967
340/621
(Continued)

FOREIGN PATENT DOCUMENTS

DE     102010040219 A1   3/2012
EP         1580539 A1   9/2005
(Continued)

*Primary Examiner* — Paul West
*Assistant Examiner* — Mark A Shabman
(74) *Attorney, Agent, or Firm* — The Ollila Law Group LLC (57) ABSTRACT

A vibratory sensor (5) includes a vibratory element (104) configured to generate a vibration signal and a meter electronics (20) coupled to the vibratory element (104) and receiving the vibration signal, with the meter electronics (20) including a gain stage (150) coupled to the vibratory element (104) and receiving the vibration signal, with the gain stage (150) amplifying the vibration signal by a predetermined gain to generate a saturated vibration signal, and a signal processor (156) coupled to the gain stage (150), with a first input (161) of the signal processor (156) receiving the saturated vibration signal and determining a vibration signal frequency from the saturated vibration signal and with a second input (162) of the signal processor (156) receiving the vibration signal and determining a vibration signal amplitude from the vibration signal.

14 Claims, 7 Drawing Sheets

(51) Int. Cl.
*G01F 1/66* (2006.01)
*G01F 1/86* (2006.01)
*G01F 1/05* (2006.01)

(52) U.S. Cl.
CPC ............ *G01N 9/002* (2013.01); *G01N 11/16* (2013.01); *G01N 2009/006* (2013.01)

(56) References Cited

U.S. PATENT DOCUMENTS

| | | | | |
|---|---|---|---|---|
| 5,743,134 | A * | 4/1998 | Dreyer | G01F 23/2967 73/1.81 |
| 5,895,848 | A * | 4/1999 | Wilson | G01F 23/2967 73/290 R |
| 6,997,052 | B2 * | 2/2006 | Woehrle | G01F 23/2967 73/290 R |
| 2002/0178787 | A1 * | 12/2002 | Matsiev | G01N 30/30 73/23.42 |
| 2005/0210954 | A1 * | 9/2005 | Raffalt | G01F 23/2967 73/1.82 |
| 2010/0161251 | A1 | 6/2010 | Angelico | |
| 2011/0179860 | A1 * | 7/2011 | Urban | G01F 23/2967 73/32 A |

FOREIGN PATENT DOCUMENTS

| | | |
|---|---|---|
| JP | 50-159323 A | 12/1975 |
| JP | 02-134058 A | 5/1990 |
| JP | 06-294728 A | 10/1994 |
| JP | 10-170568 A | 6/1998 |
| JP | 11173968 A | 7/1999 |
| JP | 2010200481 A | 9/2010 |
| JP | 2011-191091 A | 9/2011 |

* cited by examiner

VIBRATORY SENSOR AND METHOD

BACKGROUND OF THE INVENTION

1. Field of the Invention

The present invention relates to a vibratory sensor and method.

2. Statement of the Problem

Vibratory sensors, such as vibratory densitometers and vibratory viscometers, typically operate by detecting motion of a vibrating element that vibrates in the presence of a fluid material to be measured. Properties associated with the fluid material, such as density, viscosity, temperature, and the like, can be determined by processing measurement signals received from motion transducers associated with the vibrating element. The vibration modes of the vibrating element system generally are affected by the combined mass, stiffness and damping characteristics of the vibrating element and the fluid material.

Figure 1:
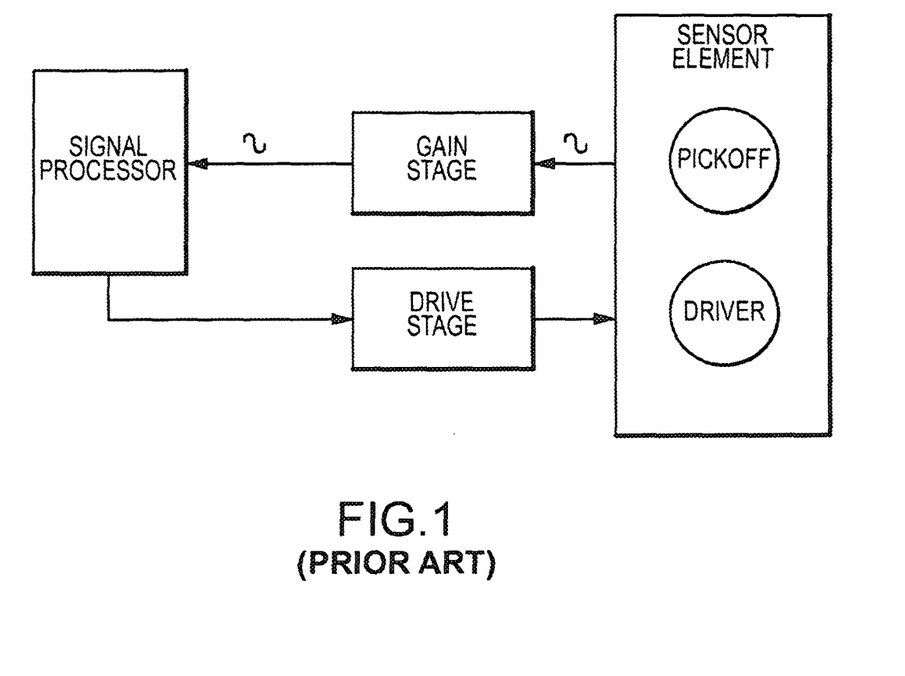
FIG. 1 shows a prior art vibratory sensor wherein a pickoff sensor generates an electronic vibration signal corresponding to a sensed vibration.

FIG. 1 shows a prior art vibratory sensor wherein a pickoff sensor generates an electronic vibration signal corresponding to a sensed vibration. The vibration signal will be substantially sinusoidal in nature. The vibration signal is received in a signal processor that measures or characterizes the vibration signal. The signal processor may comprise a coder-decoder (i.e., codec) in some embodiments. The signal processor determines both the frequency and the amplitude of the vibration signal. The frequency and amplitude of the vibration signal can be further processed to determine a density of an associated fluid, or can be processed to determined additional or other fluid characteristics.

In addition, the signal processor may generate a drive signal for the driver. The signal processor may process the vibration signal to create the drive signal. The drive signal may have a predetermined drive amplitude, wherein the predetermined drive amplitude may be fixed or varying. The drive signal may have a drive frequency that is based on the frequency and amplitude of the received vibration signal. The drive frequency may comprise a resonant frequency of the vibration sensor vibrating in a fluid to be characterized, wherein the resonant frequency is determined by adjusting the drive frequency until the amplitude of the received vibration signal is substantially at a maximum.

However, the signal processor may have a limited dynamic range and may not be capable of accurately and reliably measuring a frequency of an input signal that has a relatively small amplitude. The vibration signal has dynamic amplitude range that is significantly greater than the usable dynamic range of a typical stereo codec. In the case of a fork density meter, the dynamic range between a minimum pickoff amplitude to a maximum pickoff amplitude may be greater than 10,000, while a typical stereo codec may have a usable dynamic range of roughly 100 in order to maintain a stable closed loop drive with the frequency accuracy requirements of the system.

The prior art vibratory sensor may include a gain stage between the pickoff sensor and the signal processor. The gain implemented by the gain stage may be selected so that the vibration signal is amplified to substantially match the dynamic range of the signal processor. The frequency of the vibration signal may then be more easily and accurately measured.

The prior art vibratory sensor of FIG. 1 has drawbacks. Amplification of the vibration signal by the gain stage may enhance the ability of the signal processor to match the vibration signal to the signal processor's input and quantify the vibration signal frequency, but unfortunately this negatively affects the ability of the signal processor to quantify the vibration signal amplitude.

Figure 2:
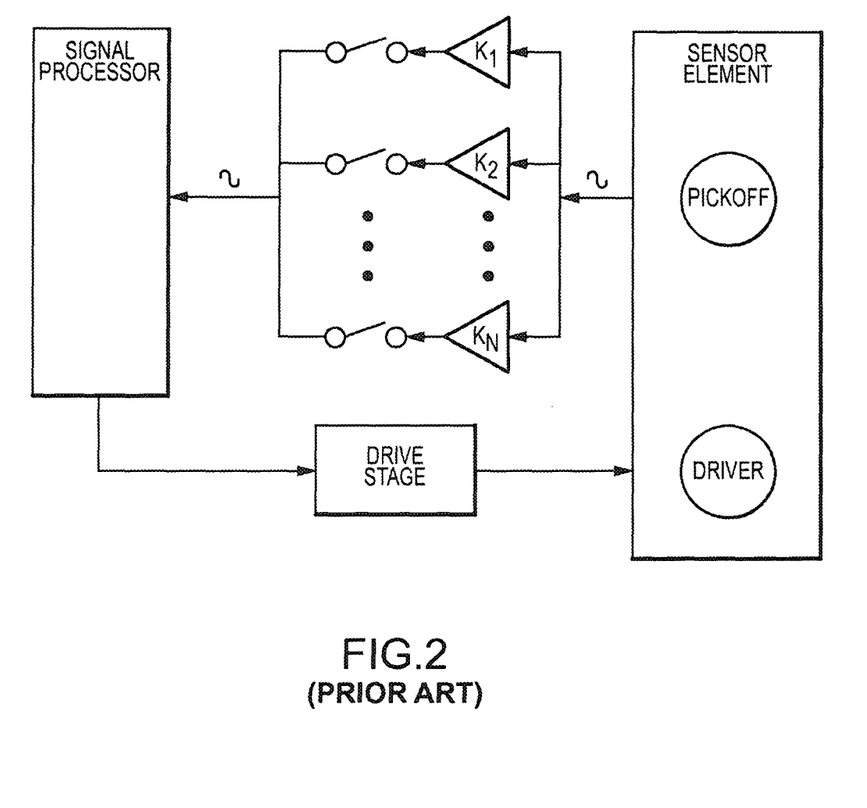
FIG. 2 shows a prior art vibratory sensor wherein the gain stage comprises multiple gain elements, wherein switches select a gain element for amplifying the vibration signal.

FIG. 2 shows a prior art vibratory sensor wherein the gain stage comprises multiple gain elements $K_1$-$K_N$, wherein switches $S_1$-$S_N$ select a gain element for amplifying the vibration signal. This prior art circuit allows the vibration signal to be amplified by more than a single gain factor.

The process of switching the gains has drawbacks, however. One problem is that the gains must be scanned dynamically during initial operation (and during slug operation) to ensure that the system remains stable at all times. Another problem is that the act of switching from one gain to the next creates nonlinearity in the measurement of both amplitude and frequency, which can result in errors in the fluid measurements generated by the prior art vibratory sensor. Yet another problem is that each gain stage has a different phase relationship from the pickoffs, which must be compensated for. In order to maintain this phase relationship, separate compensation numbers must be calculated for each usable gain stage to ensure the sensor is always operating on the predicted measurement points, as any errors in the linearization in phase from one gain to another will result in another source of measurement error.

ASPECTS OF THE INVENTION

In one aspect of the invention, a vibratory sensor comprises:
  a vibratory element configured to generate a vibration signal; and
  a meter electronics coupled to the vibratory element and receiving the vibration signal, with the meter electronics comprising:
    a gain stage coupled to the vibratory element and receiving the vibration signal, with the gain stage amplifying the vibration signal by a predetermined gain to generate a saturated vibration signal; and
    a signal processor coupled to the gain stage, with a first input of the signal processor receiving the saturated vibration signal and determining a vibration signal frequency from the saturated vibration signal and with a second input of the signal processor receiving the vibration signal and determining a vibration signal amplitude from the vibration signal.

Preferably, the saturated vibration signal comprises a substantially square-wave vibration signal.

Preferably, the second input of the signal processor is directly coupled to the vibratory element and receiving the vibration signal from the vibratory element.

Preferably, the second input of the signal processor is coupled to the gain stage and receives the vibration signal through the gain stage.

Preferably, the second input of the signal processor is coupled to a buffer and receives the vibration signal from the buffer, wherein the buffer is coupled to the vibratory element.

Preferably, the second input of the signal processor is coupled to a buffer and receives the vibration signal from the buffer, wherein the buffer is coupled to the vibratory element and wherein the buffer provides a predetermined second gain that is less than the predetermined gain used for generating the saturated vibration signal.

Preferably, the signal processor is coupled to an interface circuit, with the signal processor providing the vibration signal amplitude and the vibration signal frequency to the interface circuit for transmission to external devices.

Preferably, the signal processor is coupled to a drive circuit, with the signal processor providing the vibration signal amplitude and the vibration signal frequency to the drive circuit, with the drive circuit generating a drive signal using the vibration signal amplitude and the vibration signal frequency.

Preferably, the vibratory sensor comprises a vibratory tine sensor and the vibratory element comprises a tuning fork structure.

In one aspect of the invention, a method of operating a vibratory sensor comprises:

generating a vibration signal using a vibratory element of the vibratory sensor;

determining a vibration signal amplitude from the vibration signal;

amplifying the vibration signal by a predetermined gain and generating a saturated vibration signal; and determining the vibration signal frequency from the saturated vibration signal.

Preferably, the saturated vibration signal comprises a substantially square-wave vibration signal.

Preferably, the method further comprises providing the vibration signal amplitude and the vibration signal frequency for transmission to external devices.

Preferably, the method further comprises generating a drive signal using the vibration signal amplitude and the vibration signal frequency.

Preferably, the vibratory sensor comprises a vibratory tine sensor and with the vibratory element comprising a tuning fork structure.

DESCRIPTION OF THE DRAWINGS

The same reference number represents the same element on all drawings. The drawings are not necessarily to scale.

DETAILED DESCRIPTION OF THE INVENTION

FIGS. 3-8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 3:
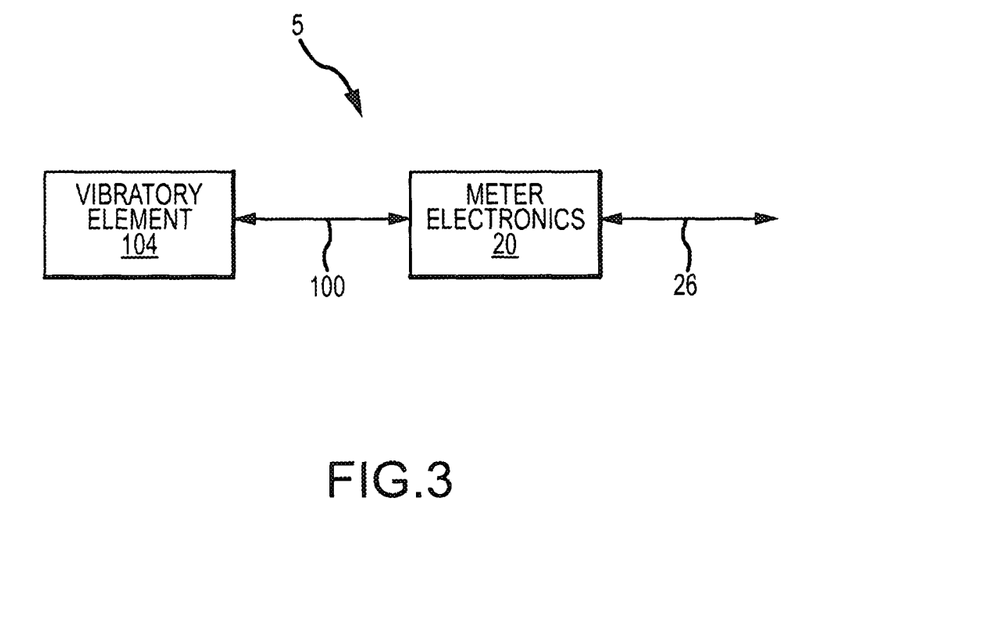
FIG. 3 shows a vibratory sensor according to the invention.

FIG. 3 shows a vibratory sensor 5 according to the invention. The vibratory sensor 5 may comprise a vibratory element 104 and meter electronics 20, wherein the vibratory element 104 is coupled to the meter electronics 20 by a lead or leads 100. In some embodiments, the vibratory sensor 5 may comprise a vibratory tine sensor or fork density sensor (see FIGS. 4 and 7-8 and the accompanying discussion). However, other vibratory sensors are contemplated and are within the scope of the description and claims.

The vibratory sensor 5 may be at least partially immersed into a fluid to be characterized. For example, the vibratory sensor 5 may be mounted in a pipe or conduit. The vibratory sensor 5 may be mounted in a tank or container or structure for holding a fluid. The vibratory sensor 5 may be mounted in a manifold or similar structure for directing a fluid flow. Other mounting arrangements are contemplated, however, and are within the scope of the description and claims.

The fluid can comprise a liquid. The fluid can comprise a gas. Alternatively, the fluid can comprise a multi-phase fluid, such as a liquid that includes entrained gas, entrained solids, multiple liquids, or combinations thereof.

The vibratory sensor 5 may operate to provide fluid measurements. The vibratory sensor 5 may provide fluid measurements including one or more of a fluid density and a fluid viscosity for a fluid, including flowing or non-flowing fluids. The vibratory sensor 5 may provide fluid measurements including a fluid mass flow rate, a fluid volume flow rate, and/or a fluid temperature. This listing is not exhaustive and the vibratory sensor 5 may measure or determine other fluid characteristics.

The meter electronics 20 may provide electrical power to the vibratory element 104 via the lead or leads 100. The meter electronics 20 may control operation of the vibratory element 104 via the lead or leads 100. For example, the meter electronics 20 may generate a drive signal and supply the drive signal to the vibratory element 104, wherein the vibratory element 104 generates a vibration in one or more vibratory components using the drive signal. The drive signal may control the vibrational amplitude. The drive signal may control the vibrational frequency. The drive signal may control the vibrational duration and/or vibrational timing.

The meter electronics 20 may receive a vibration signal or signals from the vibratory element 104 via the lead or leads 100. The meter electronics 20 may process the vibration signal or signals in order to generate a density measurement, for example. It should be understood that other or additional measurements may be generated from the vibration signal or signals.

The meter electronics 20 may process the vibration signal or signals received from the vibratory element 104 to determine a frequency of the signal or signals. The frequency may comprise a resonant frequency of the fluid. The resonant frequency may be used to determine a density of the fluid. Further, or in addition, the meter electronics may process the vibration signal or signals to determine other characteristics of the fluid, such as a viscosity or a phase shift between signals that can be processed to determine a fluid flow rate, for example. Other vibrational response characteristics and/or fluid measurements are contemplated and are within the scope of the description and claims.

The meter electronics 20 may be further coupled to a communication link 26. The meter electronics 20 may communicate a vibration signal over the communication link 26. The meter electronics 20 may process the received vibration signal to generate a measurement value or values and may communicate a measurement value or values over the communication link 26.

In addition, the meter electronics 20 may receive information over the communication link 26. The meter electronics 20 may receive commands, updates, operational values or operational value changes, and/or programming updates or changes over the communication link 26.

Figure 4:
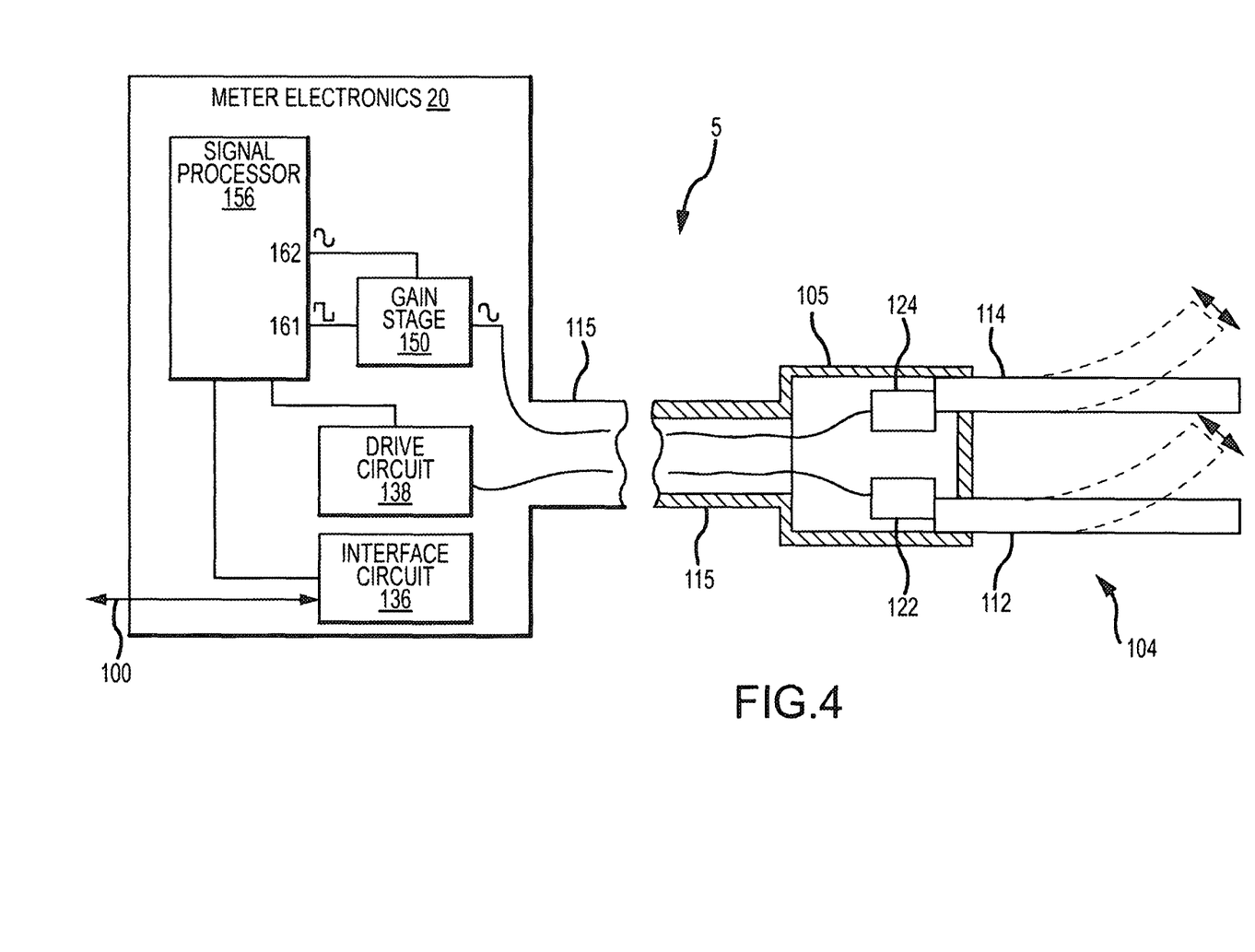
FIG. 4 shows the vibratory sensor according to an embodiment of the invention.

FIG. 4 shows the vibratory sensor 5 according to an embodiment of the invention. The vibratory sensor 5 in the embodiment shown comprises a vibratory tine sensor 5, including meter electronics 20 coupled to the vibratory element 104 by a shaft 115 in the embodiment shown. The shaft 115 may be of any desired length. The shaft 115 may be at least partially hollow and wires or other conductors may extend between the meter electronics 20 and the vibratory element 104 through the shaft 115.

The meter electronics 20 may include circuit components such as a signal processor 156, a gain stage 150, a drive circuit 138, and an interface circuit 136 in the embodiment shown. The signal processor 156 in some embodiments may comprise a stereo codec, as previously discussed.

In the embodiment shown, the drive circuit 138 and the gain stage 150 are directly coupled to the leads of the vibratory element 104. Alternatively, the meter electronics 20 may comprise a separate component or device from the vibratory element 104, wherein the drive circuit 138 and the gain stage 150 are coupled to the vibratory element 104 via the lead or leads 100, as shown in FIG. 3.

The vibratory element 104 of the vibratory sensor 5 in the embodiment shown comprises a tuning fork structure 104, wherein the vibratory element 104 is at least partially immersed in the fluid being measured. The vibratory element 104 includes a housing 105 that may be affixed to another structure, such as a pipe, conduit, tank, receptacle, manifold, or any other fluid-handling structure. The housing 105 retains the vibratory element 104, while the vibratory element 104 remains at least partially exposed. The vibratory element 104 therefore is configured to be immersed in the fluid.

The vibratory element 104 in the embodiment shown includes first and second tines 112 and 114 that are configured to extend at least partially into the fluid. The first and second tines 112 and 114 comprise elongate elements that may have any desired cross-sectional shape. The first and second tines 112 and 114 may be at least partially flexible or resilient in nature.

The vibratory sensor 5 further includes corresponding first and second piezo elements 122 and 124 that comprise piezo-electric crystal elements. The first and second piezo elements 122 and 124 are located adjacent to the first and second tines 112 and 114, respectively. The first and second piezo elements 122 and 124 are configured to contact and mechanically interact with the first and second tines 112 and 114.

The first piezo element 122 may contact at least a portion of the first tine 112. The first piezo element 122 may be electrically coupled to the drive circuit 138, with the drive circuit 138 providing a time-varying drive signal to the first piezo element 122.

The first piezo element 122 may expand and contract when subjected to the time-varying drive signal. As a result, the first piezo element 122 may alternatingly deform and displace the first tine 112 from side to side in a vibratory motion (see dashed lines), disturbing the fluid in a periodic, reciprocating manner.

The second piezo element 124 may be coupled to a receiver circuit 134 that produces a time-varying vibration response signal corresponding to the deformations of the second tine 114 in the fluid. Movement of the second tine 114 may therefore cause a corresponding electrical vibration signal to be generated by the second piezo element 124. The second piezo element 124 transmits the vibration signal to the meter electronics 20. The meter electronics 20 processes the vibration signal and may measure the vibration signal amplitude and/or the vibration signal frequency of the vibration signal.

The meter electronics 20 may include the interface circuit 136. The meter electronics 20 may transmit vibration signal characteristics to the interface circuit 136, such as a vibration signal frequency and/or a vibration signal amplitude of the vibration signal. The meter electronics 20 may transmit fluid measurements to the interface circuit 136, such as a density and/or viscosity of the fluid, among other things. Other fluid measurements are contemplated and are within the scope of the description and claims.

The interface circuit 136 may be configured to communicate with external devices. The interface circuit 136 may communicate a vibration measurement signal or signals and may communicate determined fluid characteristics to one or more external devices.

The vibratory element 104 is generally maintained at a resonant frequency, as influenced by the surrounding fluid. The vibratory element 104 is typically maintained at the resonant frequency by the drive circuit 138.

The drive circuit 138 may receive the vibration signal and may generate a drive signal from the vibration signal, and may modify characteristics of the vibration signal in order to generate the drive signal. The drive circuit 138 may modify the vibration signal to produce a desired vibrational disturbance in the fluid. The drive circuit 138 further may modify the vibration signal to compensate for the length of the leads between the meter electronics 20 and the vibratory element 104 and/or to compensate for other losses in the vibration signal, for example.

Figure 5:
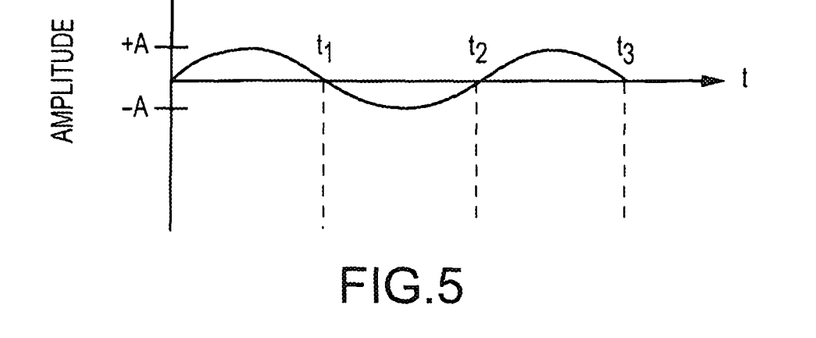
FIG. 5 is a graph of the vibration signal in an example where the amplitude is comparatively small (varying between +A and −A).

FIG. 5 is a graph of the vibration signal in an example where the amplitude is comparatively small (varying between amplitudes of +A and −A). The signal crosses the zero axis at the times $t_1$, $t_2$, and $t_3$. However, as a consequence of the small amplitude, it can be understood that determining the exact point of zero-crossing may be problematic for the signal processor 156, as the amplitude of the vibration signal changes by very little in the time instant before and after a zero crossing.

Figure 6:
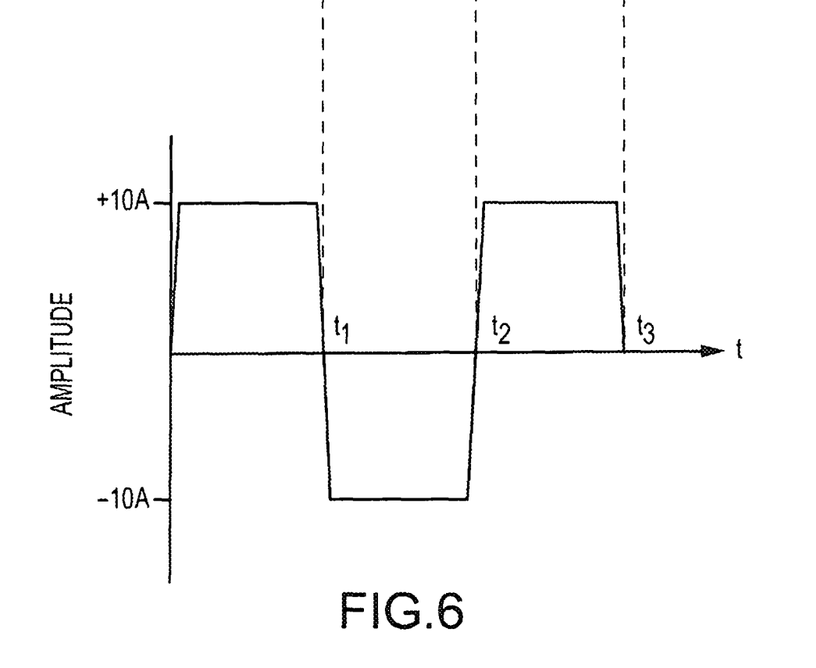
FIG. 6 is a graph of the saturated vibration signal, wherein the saturated vibration signal is greatly amplified over the vibration signal in FIG. 5.

FIG. 6 is a graph of the saturated vibration signal, wherein the saturated vibration signal is greatly amplified over the vibration signal in FIG. 5. The amplitude now varies between +10 A and −10 A in this example. The zero-crossing points are still at the times $t_1$, $t_2$, and $t_3$. However, due to the amplification, the amplitude immediately before the time $t_1$ is greatly different from the amplitude immediately after the time $t_1$, and this large change in amplitude ensures that finding the zero-crossing points will be easy and accurate. Moreover, if the vibration signal is greatly amplified, the saturated vibration signal can look like the example in FIG. 6 regardless of the amplitude of the original vibration signal.

Referring again to FIG. 4, the gain stage 150 receives the time-varying vibration signal generated by the second piezo element 124. The vibration signal comprises a substantially sinusoidal signal. The gain stage 150 implements a predetermined gain.

The gain stage 150 includes two outputs in the embodiment shown. The lower output in the embodiment shown comprises an amplified output that has been greatly amplified by the application of the predetermined gain, where the predetermined gain is a comparatively large gain. In some embodiments, the predetermined gain is chosen so as to saturate the output, wherein the outputted signal is essentially a square wave (represented by the square wave symbol at the lower output of the gain stage 150). The saturated vibration signal is ideal for determining the vibration signal frequency. The lower, amplified output of the gain stage 150 is subsequently received in a first input 161 of the signal processor 156.

The lower output of the gain stage 150 will have a fixed amplitude. More significantly, the amplitude of the saturated vibration signal enables an accurate and reliable frequency measurement. The zero-crossing points of the square wave (i.e., saturated vibration signal) will be much easier to determine than where the vibration signal is a sinusoid, and especially where the vibration signal has a small amplitude.

In contrast, the upper output of the gain stage 150 in the embodiment shown outputs a non-amplified version of the vibration signal (represented by the sinusoid symbol at the upper output of the gain stage 150). The upper, sinusoid output of the gain stage 150 is subsequently received in a second input 162 of the signal processor 156. The upper output of the gain stage 150 retains its substantially original shape. Therefore, the vibration signal can be used by the signal processor 156 for quantifying the vibration signal amplitude.

The meter electronics 20 in the figure is configured to advantageously handle large dynamic range differences by modifying the vibration signal in separate ways for each piece of information to be measured. For the purpose of better measuring the amplitude and the frequency of the vibration signal, the vibration signal is split and the vibration signal amplitude and the vibration signal frequency are individually measured using two different versions of the vibration signal. The signal processor 156 performs amplitude measurement on the essentially unchanged vibration signal. Simultaneously, the signal processor 156 receives the saturated vibration signal and the signal processor 156 performs a frequency measurement using the saturated vibration signal.

By using separate input channels of the signal processor 156, which is generally available where the signal processor 156 is implemented by a common stereo input codec, for example, the frequency and amplitude information can be separately and optimally obtained from the vibration signal. The frequency and amplitude information can be obtained without the drawbacks of using a single signal for obtaining both pieces of information. As a result, the vibration signal can be tailored to individually maximize the sensitivity of the signal processor 156 to each measurement.

The signal processor 156 and the gain stage 150 improve the measurements that are generated by the vibratory sensor 5. For the amplitude measurement, the signal processor 156 advantageously can measure amplitude across a much larger dynamic range, while measuring vibration signal frequency over a comparatively smaller dynamic range. This allows the use of only a single gain stage, and multiple gain stages and switching circuitry are not required.

Advantageously, the signal processor 156 can measure the frequency of the vibration signal without having to select a gain in advance, ensuring that regardless of the amplitude of the vibration signal, as long as it is within the functional range of the signal processor 156, a stable vibration signal frequency measurement can be generated.

Advantageously, the frequency information only has a single drive-to-pickoff phase compensation algorithm to perform, eliminating the non-linearity created by having multiple compensations for multiple gain stages.

Advantageously, the amplitude of the saturated frequency signal is predictable and is not affected by variations in the amplitude of the vibration signal, making the normalization function for the drive amplitude easier. All of these factors allow the generation of a drive signal to be much more stable and repeatable than in a prior art multiple gain stage scenario, while also generating an accurate vibration signal amplitude measurement.

Figure 7:
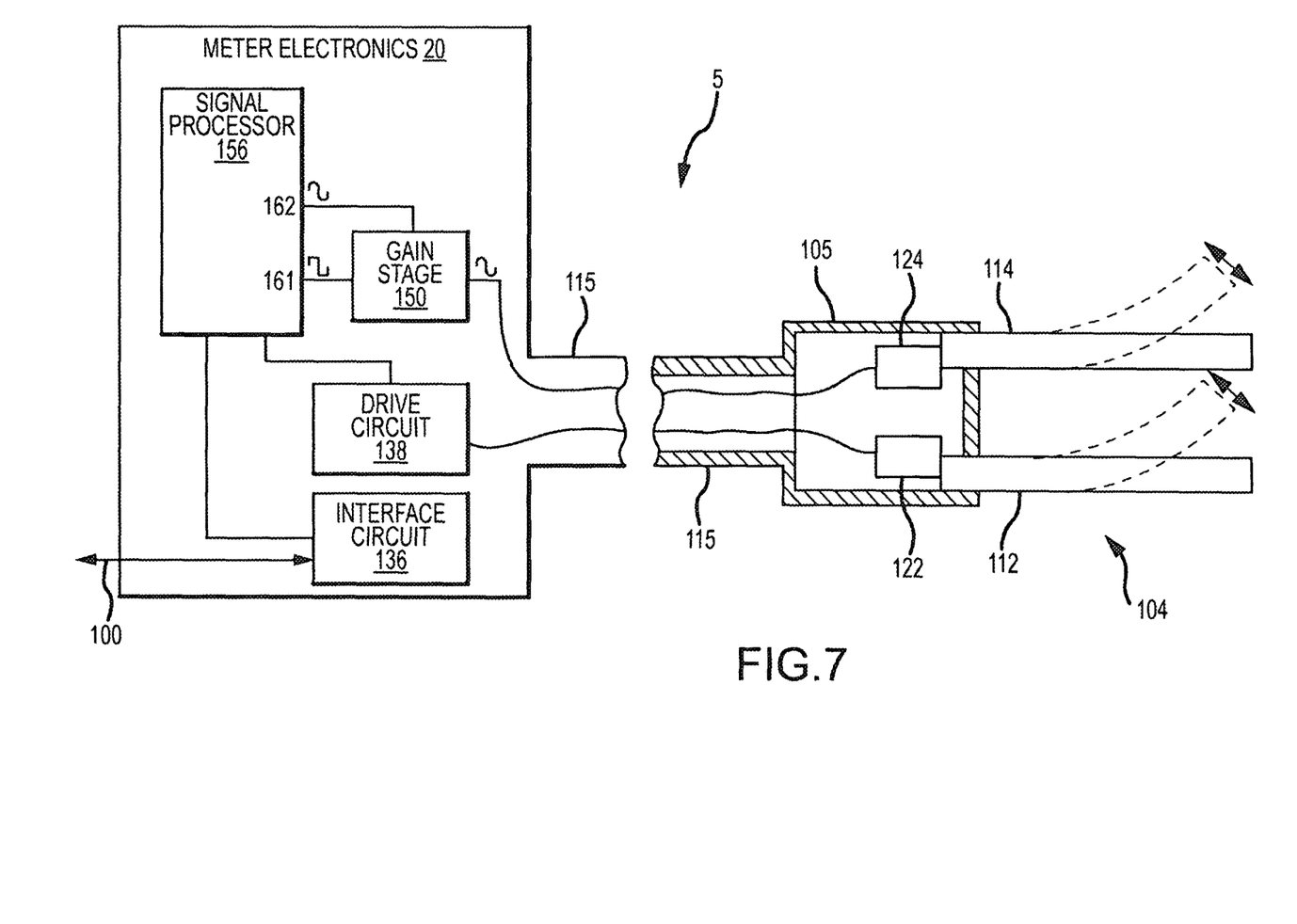
FIG. 7 shows the vibratory sensor according to another embodiment of the invention.

FIG. 7 shows the vibratory sensor 5 according to another embodiment of the invention. In this embodiment, the vibration signal is provided to the gain stage 150 and is also directly provided to the second input of the signal processor 156.

Figure 8:
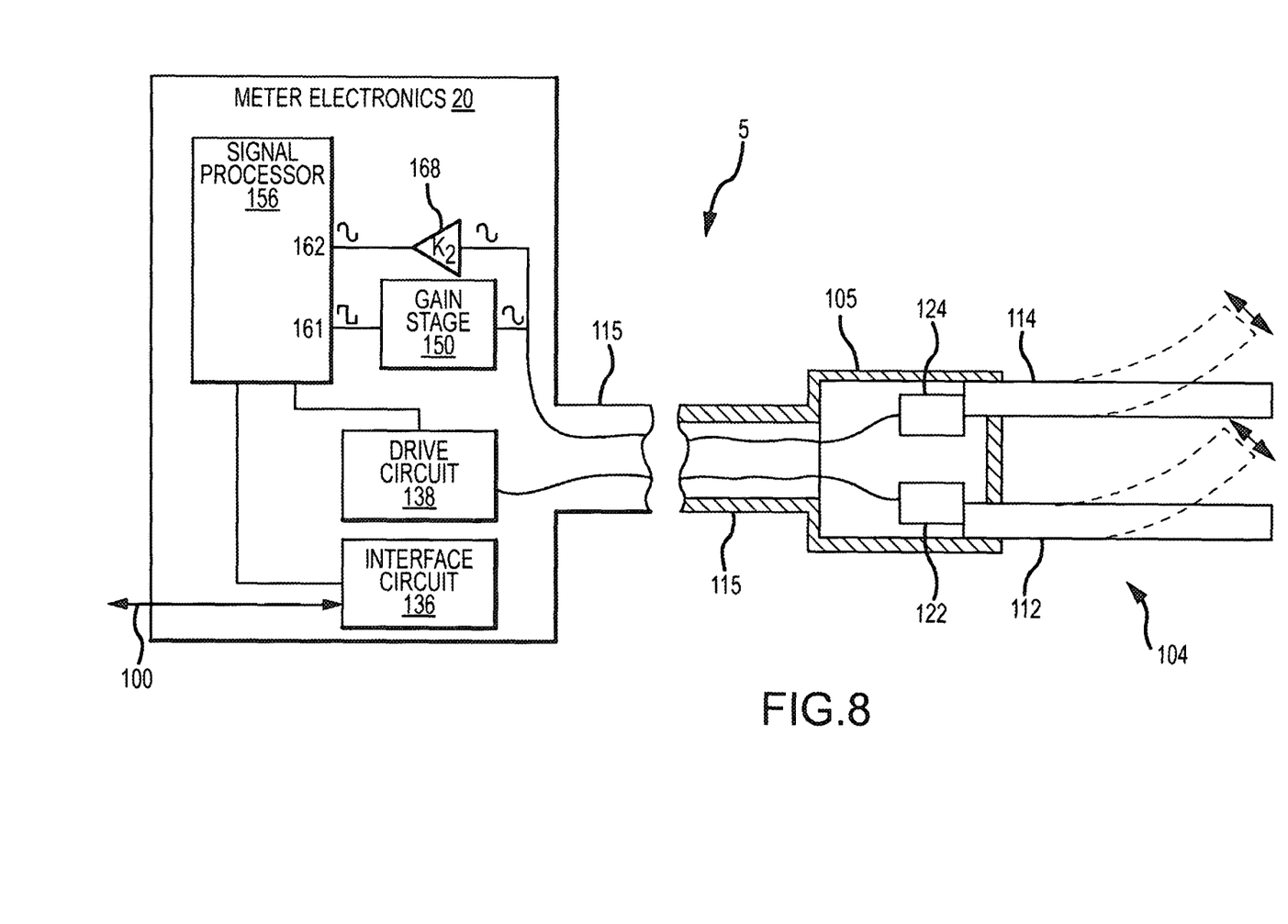
FIG. 8 shows the vibratory sensor according to another embodiment of the invention.

FIG. 8 shows the vibratory sensor 5 according to another embodiment of the invention. In this embodiment, the meter electronics 20 further includes a buffer 168. In this embodiment, the vibration signal is provided to the gain stage 150 and to the buffer 168. The buffer 168 includes a predetermined second gain $K_2$. The buffer 168 receives the vibration signal and transmits the vibration signal to the second input 162 of the signal processor 156.

The buffer 168 in some embodiments does not amplify the vibration signal (i.e., the predetermined second gain $K_2 \approx 1$). Alternatively, in other embodiments the buffer 168 may provide a modest amplification that does not saturate the vibration signal and the vibration signal remains substantially sinusoidal (i.e., the predetermined second gain $K_2 > 1$). It should be understood that the predetermined second gain is less than the predetermined gain used for generating the saturated vibration signal.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. A vibratory sensor (5), comprising:
   a vibratory element (104) configured to generate a vibration signal; and
   a meter electronics (20) coupled to the vibratory element (104) and receiving the vibration signal, with the meter electronics (20) comprising:
   a gain stage (150) coupled to the vibratory element (104) and receiving the vibration signal, with the gain stage (150) amplifying the vibration signal by a predetermined gain to generate a saturated vibration signal; and
   a signal processor (156) coupled to the gain stage (150), with a first input (161) of the signal processor (156) receiving the saturated vibration signal and determining a vibration signal frequency from the saturated vibration signal and with a second input (162) of the signal processor (156) receiving the vibration signal, the vibration signal received at the second input being unsaturated, and determining a vibration signal amplitude from the vibration signal.

2. The vibratory sensor (5) of claim 1, wherein the saturated vibration signal comprises a substantially square-wave vibration signal.

3. The vibratory sensor (5) of claim 1, with the second input (162) of the signal processor (156) being directly coupled to the vibratory element (104) and receiving the vibration signal from the vibratory element (104).

4. The vibratory sensor (5) of claim 1, with the second input (162) of the signal processor (156) being coupled to the gain stage (150) and receiving the vibration signal through the gain stage (150).

5. The vibratory sensor (5) of claim 1, with the second input (162) of the signal processor (156) being coupled to a buffer (168) and receiving the vibration signal from the buffer (168), wherein the buffer (168) is coupled to the vibratory element (104).

6. The vibratory sensor (5) of claim 1, with the second input (162) of the signal processor (156) being coupled to a buffer (168) and receiving the vibration signal from the buffer (168), wherein the buffer (168) is coupled to the vibratory element (104) and wherein the buffer (168) provides a predetermined second gain (K2) that is less than the predetermined gain used for generating the saturated vibration signal.

7. The vibratory sensor (5) of claim 1, with the signal processor (156) being coupled to an interface circuit (136), with the signal processor (156) providing the vibration signal amplitude and the vibration signal frequency to the interface circuit (136) for transmission to external devices.

8. The vibratory sensor (5) of claim 1, with the signal processor (156) being coupled to a drive circuit (138), with the signal processor (156) providing the vibration signal amplitude and the vibration signal frequency to the drive circuit (138), with the drive circuit (138) generating a drive signal using the vibration signal amplitude and the vibration signal frequency.

9. The vibratory sensor (5) of claim 1, with the vibratory sensor (5) comprising a vibratory tine sensor (5) and with the vibratory element (104) comprising a tuning fork structure (104).

10. A method of operating a vibratory sensor, with the method comprising:
generating a vibration signal using a vibratory element of the vibratory sensor;
determining a vibration signal amplitude from the vibration signal, the vibration signal being unsaturated when the vibration signal amplitude is determined;
amplifying the vibration signal by a predetermined gain and generating a saturated vibration signal; and
determining the vibration signal frequency from the saturated vibration signal.

11. The method of claim 10, wherein the saturated vibration signal comprises a substantially square-wave vibration signal.

12. The method of claim 10, further comprising providing the vibration signal amplitude and the vibration signal frequency for transmission to external devices.

13. The method of claim 10, further comprising generating a drive signal using the vibration signal amplitude and the vibration signal frequency.

14. The method of claim 10, with the vibratory sensor comprising a vibratory tine sensor and with the vibratory element comprising a tuning fork structure.

* * * * *